(12) United States Patent
McCauley et al.

(10) Patent No.: US 9,212,897 B2
(45) Date of Patent: Dec. 15, 2015

(54) CHROMATOGRAPHY COLUMN AMENABLE TO ACCURATE LENGTH DETERMINATION AND LASER ADAPTER

(75) Inventors: Edward B. McCauley, Cedar Park, TX (US); James M. Hitchcock, Pflugerville, TX (US)

(73) Assignee: Thermo Finnigan LLC, San Jose, CA (US)

( * ) Notice: Subject to any disclaimer, the term of this patent is extended or adjusted under 35 U.S.C. 154(b) by 429 days.

(21) Appl. No.: 13/369,119

(22) Filed: Feb. 8, 2012

(65) Prior Publication Data

US 2013/0199267 A1    Aug. 8, 2013

(51) Int. Cl.
| | |
|---|---|
| *G01N 30/02* | (2006.01) |
| *G01B 11/02* | (2006.01) |
| *G01S 17/88* | (2006.01) |
| *G01N 30/60* | (2006.01) |
| *G01N 30/88* | (2006.01) |

(52) U.S. Cl.
CPC ............ *G01B 11/02* (2013.01); *G01N 30/6078* (2013.01); *G01N 30/6082* (2013.01); *G01N 30/88* (2013.01); *G01S 17/88* (2013.01); *G01N 2030/889* (2013.01)

(58) Field of Classification Search
CPC ........ G01B 11/02; G01S 17/88; G01N 30/80; G01N 30/6078; G01N 30/6082; G01N 2030/889

USPC ............... 73/23.39; 356/3, 634; 702/159
See application file for complete search history.

(56) References Cited

U.S. PATENT DOCUMENTS

| | | | | |
|---|---|---|---|---|
| 4,701,869 | A * | 10/1987 | Callegari et al. | 702/158 |
| 4,935,884 | A * | 6/1990 | Hajicek | 702/159 |
| 4,968,147 | A * | 11/1990 | Shoemaker | 356/399 |
| 6,310,682 | B1 * | 10/2001 | Gavish et al. | 356/5.01 |
| 6,813,585 | B2 * | 11/2004 | Leutz et al. | 702/158 |
| 7,042,555 | B1 * | 5/2006 | Lawson | 356/3 |
| 7,537,381 | B2 * | 5/2009 | Hollander et al. | 374/142 |
| 8,326,572 | B2 * | 12/2012 | Kim et al. | 702/159 |

FOREIGN PATENT DOCUMENTS

| | | | |
|---|---|---|---|
| DE | 3816130 | * | 11/1989 |
| JP | 2000-329543 | * | 11/2000 |
| WO | WO 86/00981 | * | 2/1986 |

* cited by examiner

*Primary Examiner* — Daniel S Larkin
(74) *Attorney, Agent, or Firm* — Nicholas Cairns; Pamela Lau Kee

(57) ABSTRACT

A column used for gas chromatography (GC) is fabricated from an open tubular light guiding capillary. The light guiding capillary is suitable for transmission of optical frequencies employed in commercially available hand held laser range finders.

6 Claims, 6 Drawing Sheets

Single shot precision for 20 meter capillary
Average correction factor used to evaluate shot-to-shot error

| Cut length (m) | DLR165 reading | factor | calculated | error (mm) |
| --- | --- | --- | --- | --- |
| 20 | 14.818 | 1.349709812 | 20.000 | -0.1 |
| 20 | 14.817 | 1.349800904 | 19.999 | -1.5 |
| 20 | 14.816 | 1.349892009 | 19.997 | -2.8 |
| 20 | 14.819 | 1.349618733 | 20.001 | 1.2 |
| 20 | 14.818 | 1.349709812 | 20.000 | -0.1 |
| 20 | 14.818 | 1.349709812 | 20.000 | -0.1 |
| 20 | 14.820 | 1.349527665 | 20.003 | 2.6 |
| 20 | 14.818 | 1.349709812 | 20.000 | -0.1 |
| 20 | 14.819 | 1.349618733 | 20.001 | 1.2 |
| 20 | 14.818 | 1.349709812 | 20.000 | -0.1 |

Average factor  1.349700711

FIG. 4

Correction factor of 1.350 applied for all readings in multiple length determinations below.

Polymicro part number 1068152159 Batch #DLZ02A Mfg. Jun 22, 2006
250um nominal ID

| Cut length (m) | DLR165 reading | factor | calculated | error (mm) | error (%) |
|---|---|---|---|---|---|
| 0.1 | 0.074 | 1.351351351 | 0.0999 | -0.1 | -0.10 |
| 0.2 | 0.148 | 1.351351351 | 0.1998 | -0.2 | -0.10 |
| 0.5 | 0.372 | 1.344086022 | 0.5022 | 2.2 | 0.44 |
| 1 | 0.746 | 1.340482574 | 1.0071 | 7.1 | 0.71 |
| 2 | 1.481 | 1.350438893 | 1.9994 | -0.6 | -0.03 |
| 5 | 3.709 | 1.348072257 | 5.0072 | 7.2 | 0.14 |
| 20 | 14.806 | 1.350803728 | 19.9881 | -11.9 | -0.06 |

Replicate data set

| Cut length (m) | DLR165 reading | factor | calculated | error (mm) | error (%) |
|---|---|---|---|---|---|
| 0.1 | 0.073 | 1.369863014 | 0.0986 | -1.5 | -1.45 |
| 0.2 | 0.147 | 1.360544218 | 0.1985 | -1.6 | -0.77 |
| 0.5 | 0.372 | 1.344086022 | 0.5022 | 2.2 | 0.44 |
| 1 | 0.745 | 1.342281879 | 1.0058 | 5.8 | 0.58 |
| 2 | 1.482 | 1.349527665 | 2.0007 | 0.7 | 0.04 |
| 5 | 3.708 | 1.348435814 | 5.0058 | 5.8 | 0.12 |
| 20 | 14.82 | 1.349527665 | 20.0070 | 7.0 | 0.04 |

FIG. 5

Polymicro part number 1068152159 Batch #VEK01A Mfg. Apr 10, 2008

| Supposed length (L) | DLR165 reading | calculated | as received length |
|---|---|---|---|
| 10 | 8.033 | 10.8446 | |
| | 8.006 | 10.8081 | 10.827 |

| Cut length (m) | DLR165 reading | factor | using 1.35 calculated | error (mm) | error (%) |
|---|---|---|---|---|---|
| 10 | 7.400 | 1.351351351 | 9.990 | -10.0 | -0.10 |
| 10 | 7.405 | 1.350438893 | 9.997 | -3.2 | -0.03 |
| 10 | 7.404 | 1.350621286 | 9.995 | -4.6 | -0.05 |
| 10 | 7.413 | 1.348981519 | 10.008 | 7.6 | 0.08 |

FIG. 6

CHROMATOGRAPHY COLUMN AMENABLE TO ACCURATE LENGTH DETERMINATION AND LASER ADAPTER

BACKGROUND

Gas chromatographs (GC's) employ the use of open tubular capillary columns in order to affect a separation of chemical constituents contained in a sample mixture. The history of the development of modern capillary columns can be found in an article by S. R. Lipsky entitled "The Fused Silica Glass Capillary Column for Gas Chromatography—The Anatomy of a Revolution" Journal of Chromatography Library, Volume 32, 1985, pages 257-282. Since this time, the "anatomy" of GC columns has remained largely unchanged.

Accuracy, and more importantly, precision of the flow rate through a capillary column is necessary for repeatable retention times, critical to component identification. The small bore and high pressure drop of these capillary columns result in small volumetric flow rates, which are difficult to precisely control when closing the control loop using a flow sensing element. Since this is the case, a calculated flow is generally used instead by closing the control loop using a pressure sensing element. This is commonly referred to as "Electronic Pressure Control" or EPC. The relationship of flow to pressure is given by the well known Poiseuille equation using prior knowledge of the gas viscosity, column dimensions, inlet and outlet pressures.

$$\frac{dV}{dT} = \frac{\pi r_4}{16\eta L}\left(\frac{(p_i^2 - p_o^2)}{p_o}\right) \quad \text{Equation 1}$$

where:
$P_i$ inlet pressure
$P_o$ outlet pressure
L is the length of the column
$\eta$ is the viscosity of the gas
r is the column internal radius As can be seen in Equation 1 above, the column radius term is raised to the fourth power. It is thus desirable that the actual radius is known to a high degree of accuracy in order to avoid multiplicative errors. This is especially important to achieve the highest analytical reproducibility column to column and instrument to instrument. The stated internal diameter (2× radius) as reported from a column manufacturer is a "nominal" one and subject to inaccuracy.

Methods are known in the art for more accurately determining the column radius (and thus the diameter) by measuring column flow rate accurately in accordance with Equation 1, using a high enough pressure drop which results in a large enough flow to accurately be measured. Once the radius is known, lower pressures can then be used to set the column flow through calculation also in relation to Equation 1.

Another known technique for measuring the column internal diameter involves measuring the retention time of an "un-retained" peak to determine average linear velocity. This technique does not require an accurate flowmeter, as time can be measured accurately. Regardless of which of these techniques is used for determining column ID, it is necessary to know in advance the accurate column length in order to make the determination.

Capillary column lengths are subject to an initial error from the manufacturer as well as operator induced uncertainties. As a matter of routine practice, columns are trimmed in length in order to re-establish adequate performance. The column end inserted into a detector and more particularly the end inserted into a chromatograph inlet need to be trimmed when fouled with non-volatile sample matrix, particles from septa or ferrules, oxidation from excessive heat and oxygen exposure. Trimming GC columns in this manner necessitates the keeping of a log book which notes the total remaining column length so that proper values can be entered into the EPC control algorithm. In addition, the logbook must associate this information with each particular column so that columns may be disposed of when they reach a lower practical length. Even if a logbook is maintained, the error in cut lengths can stack up, eventually resulting in a column with an inaccurate known length. Measuring the column length by the use of a ruler is impractical for all but the shortest GC columns, as often columns are in excess of 15 meters so that adequate separation can be accomplished. It is also impractical to unwind these columns from their supplied cages as doing so can damage the fragile column.

SUMMARY

For applications that require knowing accurate column dimensions, the present invention provides a device and method for accurately measuring a GC column length, without the need for maintaining a log book or physically dismounting a column from its cage. The system disclosed easily measures the length of a capillary column for purposes of determining a minimal practical length.

A column used for gas chromatography (GC) is fabricated from a light guiding open tubular capillary. The light guiding capillary is suitable for transmission of optical frequencies employed in commercially available hand held digital range finders. A laser rangefinder adapter and method are also disclosed, which allow measuring a GC column length using a standard off-the-shelf range finder.

BRIEF DESCRIPTION OF THE DRAWINGS

FIG. 4 shows shot-to-shot precision and accuracy data for a 20 meter length of light guiding capillary.

FIG. 5 shows data sets for replicate measurements of multiple length light guiding capillaries.

FIG. 6 shows data obtained from a light guiding capillary from a differing lot number.

DETAILED DESCRIPTION

Figure 1:
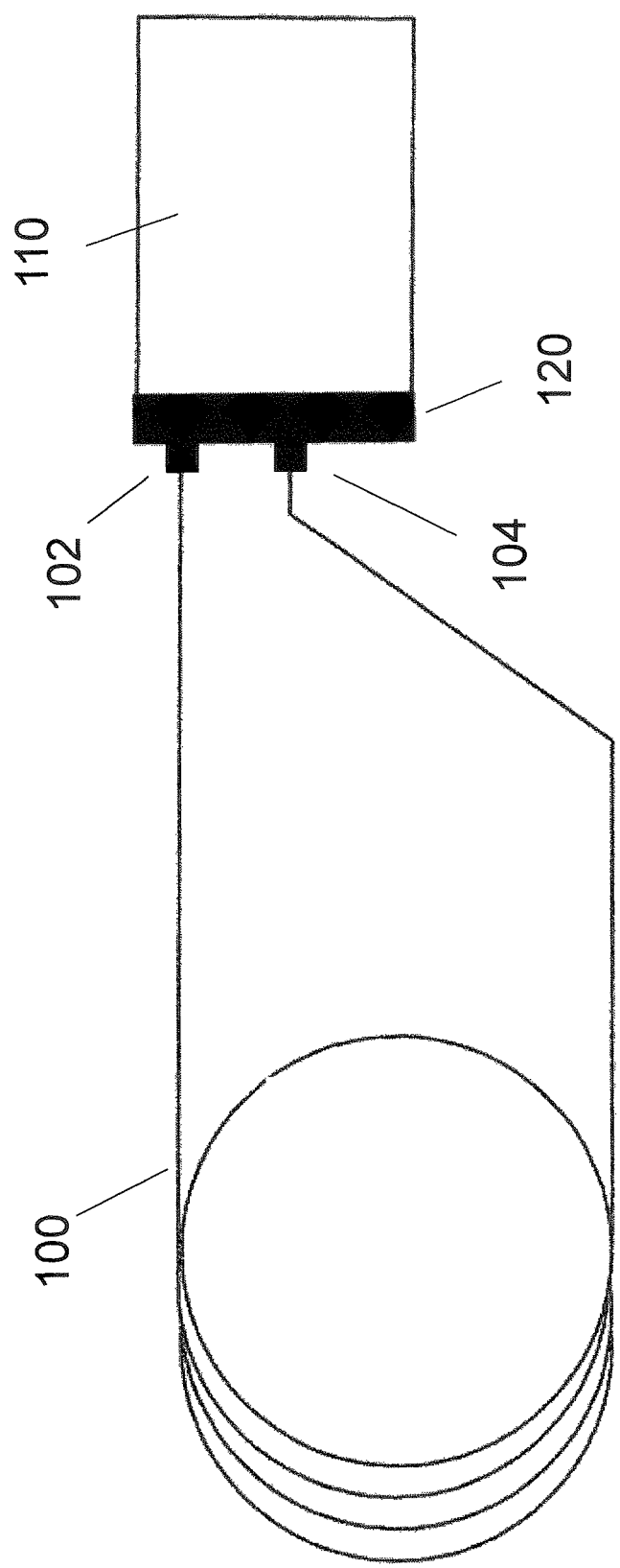
FIG. 1 illustrates a functional block diagram of the system in use according to the invention.

FIG. 1 illustrates a functional block diagram of the system in use according to the invention. A range finder 110 is positioned proximate a light guiding capillary 100. The range finder 110 operates in the range of 630 and 670 nm, e.g. Bosch DLR165K in the illustrative example, has an operable wavelength of 635 nm and a range from 5 centimeters to 50 meters in open air. A column adapter 120 which can be fabricated from injection molded rubber such as silicone, neoprene and like materials has a column adapter port 102 in light communication with the laser output of rangefinder 110. In addition, the column adapter 120 has an adapter port 104 in light communication with a detector input of rangefinder 110. The adapter 120 may also include a capillary guide means, such as short glass capillaries sealed at one end or clear plastic tubes sealed at one end, located within adapter ports 102, 104.

These can act to keep light guiding capillary 100 in proper axial alignment and distance from the input and output of rangefinder 110, as well as acting as a lens element for proper dispersion at the detector end.

The adapter 120 is preferably made of a material which is optically opaque at the intended wavelength of use in order to eliminate backscattered laser light from directly entering the receiving end of rangefinder 110. Adapter 120 may be constructed as a rectangular tubular member. It is to be understood that laser rangefinder 110 can be a unit purchased directly as is available for example in home improvement stores, or it can be an OEM device with a built in calibration factor as will be described. The OEM device may also include either separately, or as an integral part of the design, the adapter 120.

The rangefinder 110 of FIG. 1 can be an off-the-shelf device. In general, laser rangefinders act by sending a pulse of laser radiation to a distant object and measure the time for the pulse of radiation to arrive back at a detector. Prior knowledge of the speed of light in air along with the propagation time allows for the device to calculate an accurate distance. For the DLR165K example, the open air measurements are accurate to within +/−1.5 mm. Optical wavelengths in the visible or invisible spectrum may be used, provided the substrate material 150 of FIG. 2 is capable of transmission.

The off-the-shelf rangefinder 110 of FIG. 1 can be configured to transmit laser radiation through a silica tubular member, such as light guiding capillary 100, using the adapter 120. In this case, the rangefinder will report a length which can be corrected with a proper multiplier. If for example the propagation delay were equivalent to air, a capillary of e.g. twenty meters in length would be reported as being ten meters long. This is due to the fact that the light travels through the tube directly to the detector rather than reflecting off a distant object and covering the same distance twice. A correction factor of 2.000 in this example would allow measuring column lengths twice the rated limit of the rangefinder. In reality, the silica matrix of the light guiding capillary 100 causes a longer propagation delay than that of air, and so the effective range is less than twice.

For the examples illustrated in the Figures, a correction factor of 1.350 applied to the rangefinder readings result in the actual column length. Thus, a rangefinder limited to an output of fifty meters will be capable of measuring a column length of 67.5 meters. Rangefinders providing longer distance measurements will allow measuring columns longer than this.

Figure 2:
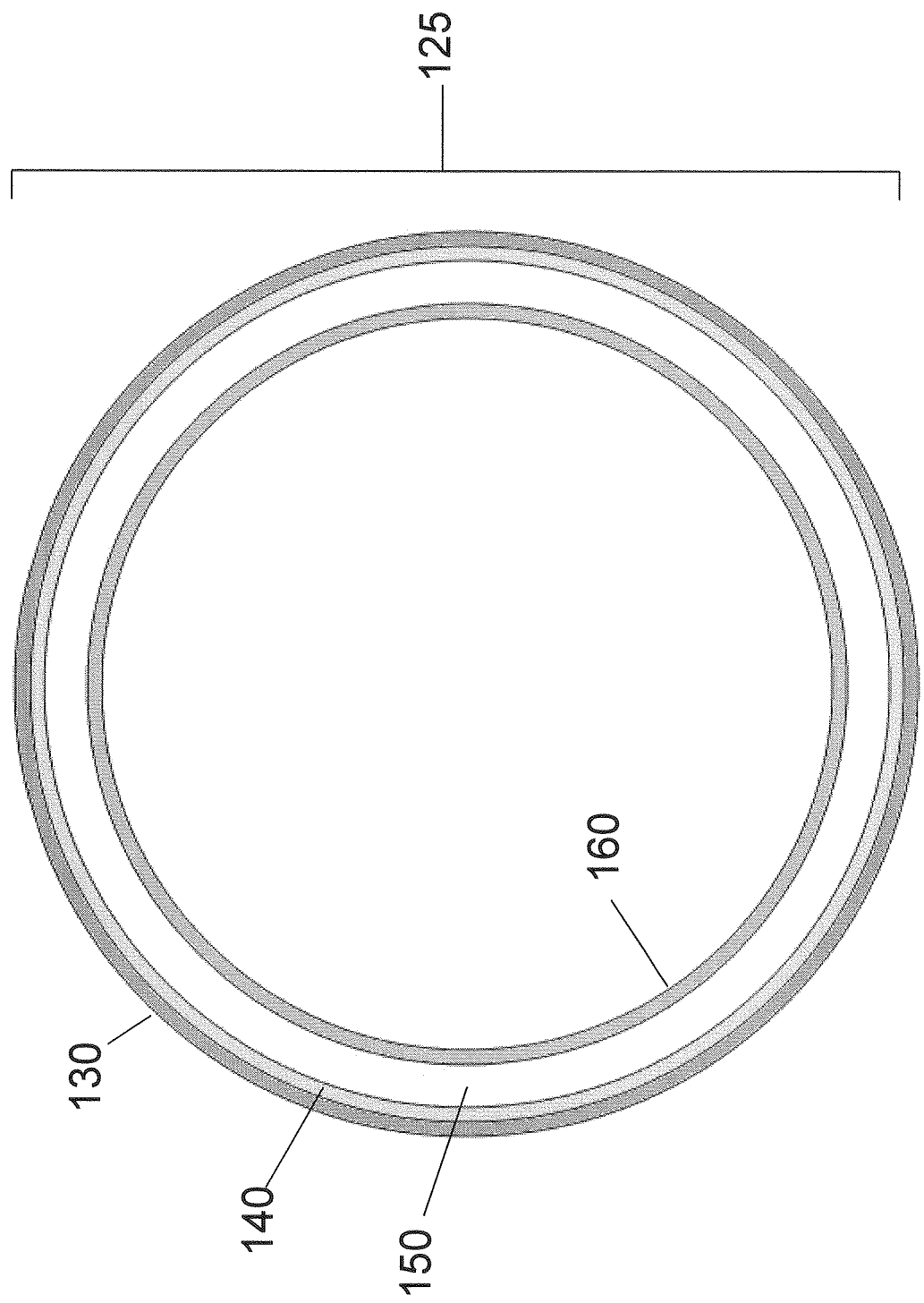
FIG. 2 illustrates a cross-section of the capillary according to the invention.

FIG. 2 illustrates a cross-section of a GC capillary column fabricated in accordance with an embodiment of the present invention. A fused silica light guiding capillary tube 125 such as is used in evanescent wave detection, e.g. Poly Micro LTSP250350, is coated internally with a cross bonded stationary phase 160, in accordance with coating techniques commonly employed in the art.

In this non-limiting illustrative embodiment, a substrate layer 150 is fused silica. An outer second layer of doped silica cladding 140 is positioned over the substrate 150 and a protective outer coating 130 of polyimide, aluminum or other known materials for protecting fused silica capillaries. A necessary requirement for efficient total internal reflection (TIF) is that the refractive index of silica substrate 150 be higher than that of the surrounding layers 140 and 160. Doped silica layer 140 can therefore comprise a fluorine doped silica.

Capillary tubes are drawn from tubular quartz "preforms" and fluorine doped preforms are commonly available for fabrication into capillaries. Quartz tubular preforms of this nature can be coated externally as well as internally with layers of lower index materials. If the stationary phase 160 has a higher index than substrate 150, a second doped silica layer (not illustrated) may be placed between layers 150 and 160. It is understood that additional layers or surface treatments may also be incorporated between the stationary phase 160 and the adjacent underlying layer for proper surface chemistry consistent with efficient chromatography and cross linking and bonding of stationary phase 160.

Figure 3:
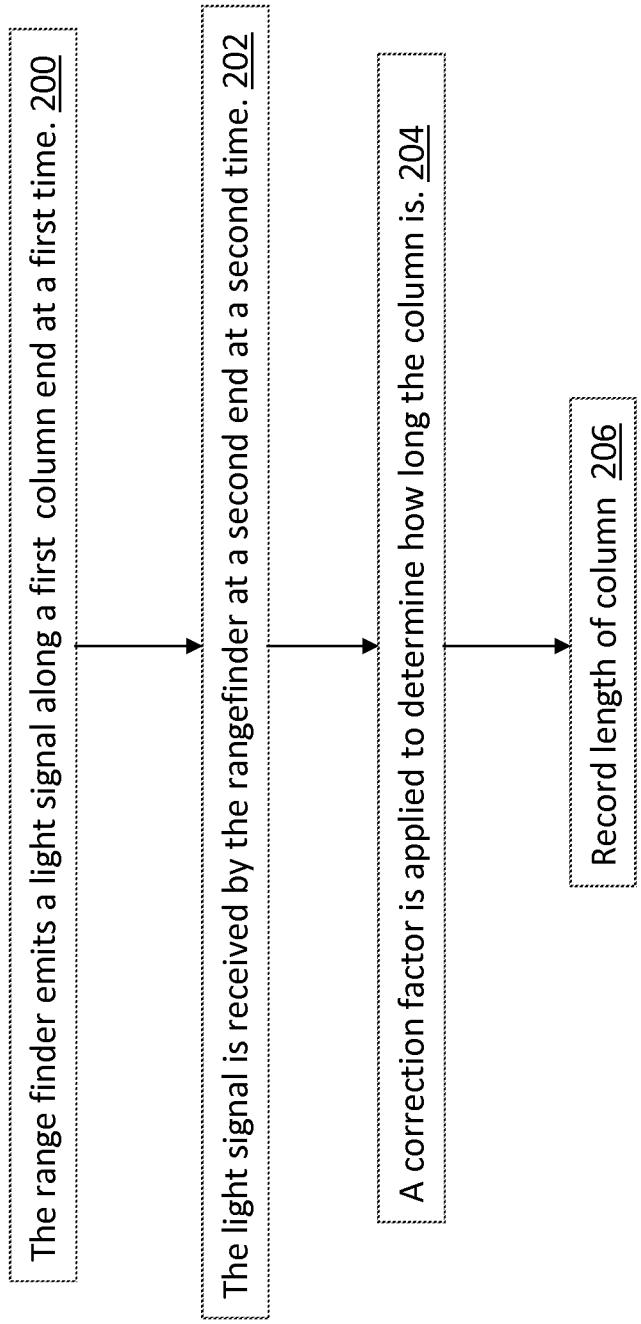
FIG. 3 is a process flowchart according to the invention.

FIG. 3 is a process flowchart according to the invention. In step 200, the range finder emits a light pulse along the length of the column at a first time. In step 202, the light pulse is received by the range finder at a second time. In step 204, a correction factor is applied to determine how long the column is. In step 206, the length of the column is recorded. The correction factor applied in step 204 may be known in advance, or it can be measured with an initial known column length.

FIG. 4 illustrates accuracy and precision data for a twenty meter length of a light guiding capillary. These data represent information gathered from multiple measurements from a single cut capillary attached to a laser range finder. The average correction factor was used to calculate an actual length. As can be seen in the data, a high degree of precision is possible.

FIG. 5 illustrates data obtained when measuring multiple known lengths of a light guiding capillary. Seven differing lengths were measured in replicate with a maximum absolute error less than 2 cm for a twenty meter capillary.

FIG. 6 illustrates data obtained from a separate lot number and manufacturing date of capillary tubing ordered as a ten meter length. The "as received" length was first measured in accordance with the method used in FIG. 5. This gave an average determination of 10.83 meters. When uncoiled and measured, the actual length was found to be 10.83 meters. This capillary was then cut to a length of ten meters and measured four times using the rangefinder method. The maximum absolute error was 1 cm.

We claim:

1. A method for determining the length of a capillary gas chromatography column fabricated from a light guiding capillary tube material using an optical rangefinder, the method comprising:
    coupling first and second ends of the gas chromatography column to an input and an output of the optical rangefinder using an adapter, the gas chromatography column being coiled;
    operating the rangefinder to determine an uncorrected length of the column; and
    calculating a corrected column length from the uncorrected length and from a correction factor, the correction factor being empirically determined by measurement of a length of a column of known length fabricated from the light guiding capillary tubing using the optical rangefinder.

2. A method as in claim 1, wherein the rangefinder is a digital rangefinder.

3. A method as in claim 1, wherein the rangefinder operates within the visible light spectrum.

4. A method as in claim 1, wherein the rangefinder operates within the invisible light spectrum.

5. A method as in claim 1, wherein the rangefinder operates at 635 nm.

6. A method as in claim 1, wherein the rangefinder operates in the range of 630 and 670 nm.

* * * * *